United States Patent [19]

Tanaka et al.

[11] Patent Number: 4,592,773
[45] Date of Patent: Jun. 3, 1986

[54] SUBSTITUTED PROPARGYLOXYACETONITRILE DERIVATIVES, PROCESS FOR PRODUCTION THEREOF, AND HERBICIDE AND AGRICULTURAL-HORTICULTURAL FUNGICIDE COMPRISING SAID DERIVATIVES AS ACTIVE INGREDIENTS

[75] Inventors: Yoshinori Tanaka, Yokohama; Kazuya Sakai, Mobara; Toshiyuki Kouno, Chosei; Mithuo Itakura; Koichi Takeuchi, both of Mobara; Yuji Enomoto, Yokohama; Hitoshi Shimotori, Yokohama; Shunichi Inami, Yokohama; Yoshikata Hojo, Yokohama; Masahiro Sakakibara, Kamakura, all of Japan

[73] Assignee: Mitsui Toatsu Chemicals, Incorporated, Tokyo, Japan

[21] Appl. No.: 762,382

[22] Filed: Aug. 5, 1985

[30] Foreign Application Priority Data

Aug. 10, 1984 [JP] Japan .................. 59-166316
Nov. 28, 1984 [JP] Japan .................. 59-249627

[51] Int. Cl.$^4$ .................. A01N 43/30; A01N 37/34; C07C 121/80
[52] U.S. Cl. .................. 71/88; 71/105; 558/392; 514/466; 514/521; 549/436
[58] Field of Search .............. 260/465 D; 71/105, 88; 549/436; 514/466, 521

[56] References Cited

U.S. PATENT DOCUMENTS 4,447,446  5/1984  Kay et al. .................. 514/521

Primary Examiner—Dolph H. Torrence
Attorney, Agent, or Firm—Fisher, Christen & Sabol

[57] ABSTRACT

Substituted propargyloxyacetonitrile derivative represented by the general formula (I)

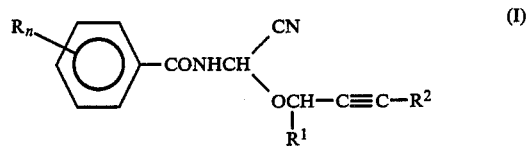

wherein R represents a hydrogen atom, a halogen atom, a lower alkyl group, a lower haloalkyl group, a lower alkoxy group, a methylenedioxy group, a nitro group or a cyano group, n represents an integer of 1 to 5 and when n is an integer of 2 or more, R's may be identical or different, $R^1$ represents a hydrogen atom or a lower alkyl group, and $R^2$ represents a hydrogen atom, a lower alkyl group, a lower haloalkyl group or a halogen atom, provided that $R^1$ and $R^2$ are not simultaneously hydrogen atoms.

The compounds have herbicidal and fungicidal activities.

18 Claims, No Drawings

SUBSTITUTED PROPARGYLOXYACETONITRILE DERIVATIVES, PROCESS FOR PRODUCTION THEREOF, AND HERBICIDE AND AGRICULTURAL-HORTICULTURAL FUNGICIDE COMPRISING SAID DERIVATIVES AS ACTIVE INGREDIENTS

This invention relates to substituted propargyloxyacetonitrile derivatives represented by the following general formula (I)

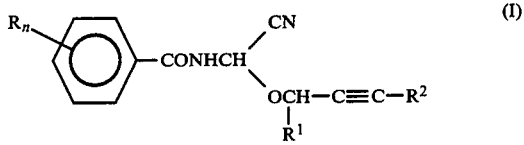

wherein R represents a hydrogen atom, a halogen atom, a lower alkyl group, a lower haloalkyl group, a lower alkoxy group, a methylenedioxy group, a nitro group or a cyano group, n represents an integer of 1 to 5 and when n is an integer of 2 or more, R's may be identical or different, $R^1$ represents a hydrogen atom or a lower alkyl group, and $R^2$ represents a hydrogen atom, a lower alkyl group, a lower haloalkyl group or a halogen atom, provided that $R^1$ and $R^2$ are not simultaneously hydrogen atoms;
a process for production thereof, and to a paddy herbicide or an agricultural-horticultural fungicide comprising such a derivative as an active ingredient.

Much work has previously been done on agriculturally and horticulturally useful amide derivatives, and many compounds having characteristic biological activities have been found and come into practical applications. For example, with regard to substituted benzamide derivatives, ethyl-N-benzoyl-N-(3,4-dichlorophenyl)-2-aminopropionate (benzoylpropethyl) is known as a herbicide and 2-methyl-N-(3-isopropoxyphenyl)benzamide (mepronil) is known as a fungicide. GB Nos. 2,095,237 and 2,094,786 disclose herbicides and fungicides comprising amide-substituted acetonitrile derivatives. GB No. 2,094,786 describes allyloxyacetonitrile derivatives, but fails to give any description of substituted propargyloxyacetonitrile derivatives. Furthermore, GB No. 2,094,786 refers to the use of the allyloxyacetonitrile derivatives as fungicides and herbicides. In this patent, the herbicidal activities of the herbicides by pre-emergence and post-emergence applications are illustrated, and their phytotoxicity on sugar beet, crucifers, cotton, soybean, corn, wheat and rice is tested. As crops having selectivity, sugar beet, crucifers, lettuce and peas are mentioned, and it is clearly stated that these derivatives are useful compounds for crops of the families Compositae and Legminosae. However, no selectivity was found for rice, and these compounds are regarded as inapplicable to rice. Many herbicides such as amide compounds, thiol carbamate compounds and diphenyl ether compounds have been developed and come into practice use for application to paddies, but their performances have not proved to be sufficient. Butachlor, an amide compound, is applied about the time of seedling, but its phytotoxicity to rice dependent upon temperature conditions and the like is always a problem. Molinate, a thiolcarbamate compound, has fish toxicity, and its use is restricted. Benthiocarb causes phytotoxicity to rice under soil reducing conditions. The diphenyl ether compounds are used about the time of seedling as is Butachlor, but if the time of treatment is retarded, their activity is reduced extremely. Because of excellent performances in some aspect, these herbicides actually gain widespread acceptance. But their defects and problems have gradually become actual, and there has been a strong desire for a paddy herbicide which is easier to use and has an excellent performance.

The compounds described in GB No. 2,094,786 are described as having an efficacy against vine downy mildew and tomato late blight as a fungicide. Captafol, TPN, captan and dithiocarbamate-type chemicals have generally been used widely against late blight and downy mildew of various crops, and have contributed to increased harvests. However, these compounds are mainly have a preventive effect on these plant diseases, and cannot at all be expected to have a curative effect. Thus, they have the defect that their effects cannot be fully expected in crops which have already been infected by these diseases. When application of chemicals for controlling plant diseases is actually considered, the time of application of these chemicals is more or less after plant diseases have occurred, and it is difficult for these compounds to control plant diseases completely. In an attempt to remove such defects, extensive work have been done on new controlling agents, and N-phenylalanine ester derivatives, such as metalaxyl [N-(2,6-dimethylphenyl)-N-(2'-methoxyacetyl)-alanine methyl ester], which also have an excellent curative effect have been developed and gradually gained practical acceptance throughout the world. However, the problem with these N-phenylalanine ester derivatives is that fungal strains resistant to these compounds are already in existence.

It is an object of this invention to remove the defects of the prior art discussed above, and to provide compounds having very good properties as a paddy herbicide and an agricultural-horticultural fungicide, a process for production thereof and an agent for controlling weeds and an agent for controlling noxious microorganisms.

Specifically, it is an object of this invention to provide compounds having a wide range of applicability, which as a herbicide, have a broad range of the suitable time of application to paddies with low phytotoxicity to rice and low fish toxicity, and as a fungicide, have both a preventive and a curative effect on late blight and downy mildew of various crops and an excellent controlling effect on soil diseases of various crops such as seedling damping off.

The present inventors have made extensive investigations on amide-substituted acetonitrile derivatives in order to achieve the above objects, and have found that substituted propargyloxyacetonitrile derivatives possess biological properties which cannot be anticipated from the compounds disclosed in the above-cited patent documents, and have a broad range of the suitable time of application with low phytotoxicity to rice and low fish toxicity as a paddy herbicide and both a preventive and a curative effect on late blight and downy mildew of various crops and an excellent control effect on soil diseases of various plants, such as seedling damping off, as a fungicide. This discovery has led to the prevent invention.

The substituted propargyloxyacetonitrile derivatives of this invention are novel compound represented by the following general formula (I)

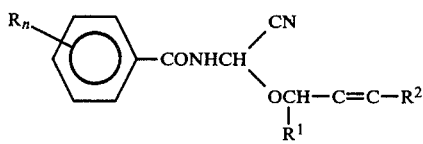

(I)

wherein R represents a hydrogen atom, a halogen atom, a lower alkyl group, a lower haloalkyl group, a lower alkoxy group, a methylenedioxy group, a nitro group or a cyano group, n represents an integer of 1 to 5 and when n is an integer of 2 or more, R's may be identical or different, $R^1$ represents a hydrogen atom or a lower alkyl group, and $R^2$ represents a hydrogen atom, a lower alkyl group, a lower haloalkyl group or a halogen atom, provided that $R^1$ and $R^2$ are not simultaneously hydrogen atoms.

The present inventors have further worked extensively on a process of producing the substituted propargyloxyacetonitrile derivatives of general formula (I) in order to overcome the defects of the prior art, and have consequently found a method by which these compounds can be obtained in high yields by substantially a shorter process.

Thus, according to this invention, there is provided a process for producing the substituted propargyloxyacetonitrile derivatives of general formula (I), which comprises reacting an acid chloride represented by the following general formula (II)

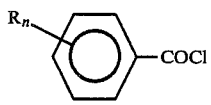

(II)

wherein R and n are as defined hereinabove, with aminoacetonitrile to obtain an acylaminoacetonitrile represented by the general formula (III)

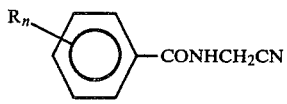

(III)

wherein R and n are as defined above, treating the resulting compound with a halogenating agent to obtain an intermediate represented by the following general formula (IV)

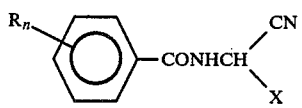

(IV)

wherein R and n are as defined above, and X represents a halogen atom,
and reacting the intermediate with a substituted propargyl alcohol of the general formula (V)

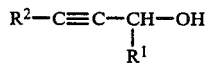

(V)

wherein $R^1$ and $R^2$ are as defined above.

This process of the invention is shown by the following reaction scheme.

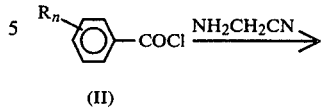

(II)

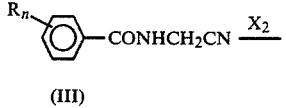

(III)

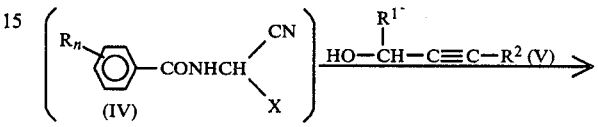

(IV)

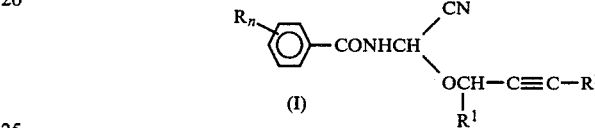

(I)

This process will be described in more detail.

First, the acid chloride (II) is reacted with aminoacetonitrile to obtain the acylaminoacetonitrile (III).

The acylaminoacetonitrile (III) is treated with a halogenating agent in a suitable solvent to obtain the halogenated intermediate (IV). Examples of the solvent may include aliphatic halogen compounds such as dichloromethane, chloroform, carbon tetrachloride and 1,4-dichloroethane, aliphatic carboxylic acid esters such as methyl acetate, ethyl acetate, isopropyl acetate and ethyl propionate, and carbon disulfide. The use of the aliphatic carboxylic acids, particularly ethyl acetate, gives good results. Bromine, chlorine, phosphorus oxychloride, sulfuryl chloride, and phosphorus tribromide can, for example, be used as the halogenating agent. The reaction temperature is 0° to 120° C., preferably room temperature. This reaction may be carried out in an atmosphere of an inert gas. Since the halogenated intermediate (IV) is unstable, it is used immediately after preparation.

The halogenated compound (IV) is then reacted with the substituted propargyl alcohol (V). This reaction can be carried out in the presence of an acid acceptor. Examples of the acid acceptor include organic bases such as triethylamine, dimethylaniline and pyridine, and inorganic bases such as ammonia, potassium carbonate, sodium carbonate, sodium hydrogen carbonate, sodium hydroxide and ammonium carbonate. This reaction is preferably carried out in a solvent or a diluent. Pyridine can be used both as the solvent and the acid acceptor. Since the intermediate has no good heat stability, it is undesirable to carry out this reaction at too high temperatures. Furthermore, since it is an exothermic reaction it is desirably carried out with cooling. At low temperatures, the reaction intermediate is liable to precipitate, and the rate of the reaction becomes so slow that it is not practical. Desirably, the reaction is carried out at −30° to 50° C., preferably at −20° to 20° C. The desired substituted propargyloxyacetonitrile derivative (I) can be isolated and purified easily by a conventional method such as recrystallization and column chromatography.

The present invention further provides a paddy herbicide and an agricultural-horticultural fungicide comprising a substituted propargyloxyacetonitrile derivative of general formula (I) as an active ingredient.

For use as a paddy herbicide, the suitable rate of application of the compound is usually 0.1 to 100 g, desirably 0.5 to 25 g, per are although it varies depending upon the type of weeds to be controlled, the stage of their growth, the type of a formulation to be applied, the method of its application and various environmental conditions. The herbicidal activity of the compound of this invention is characteristically strong against gramineous weeds, but it also shows a strong suppressing effect on other weeds although to varying degrees depending upon the types of the weeds. It shows a particularly strong inhibiting effect on weeds of the family Cyperaceae (umbrella plants), such as *Cyperus difformis* Linnaeus (small flower unbrella plant). This property advantageously acts when one contemplates the application of this compound as a mixture with a conventional chemical having weak activity on gramineous weeds, or by mixed application by tank mixing, for example.

The suitable time of application of the compound of this invention is broad ranging from the pre-emergence period of weeds to their growing stage. The compounds of this invention have a much broader range of the suitable time of application than known amide-type compounds such as Butachlor or thiol carbamate compounds such as Benthiocarb, and can become herbicides that are little restricted in the time of application and are easy to use. The practical doses of the compound of this invention which will produce herbicidal activity on barnyard grass naturally differ depending upon the time of application. But while benthiocarb or Butachlor produces only an insufficient effect on barnyard grasses in the 3.5-leaf stage at the practical doses, the compounds of this invention exhibit fully practical activity in doses less than the practical doses. The compounds of this invention cause vary little phytotoxicity to transplanted rice when applied to any growth stage.

When used as an agricultural-horicultural fungicide, the compounds of this invention are effective not only against late blight and downy mildew of various crops caused by Phycomycetes but also against various diseases caused by various plant pathogenic fungi. Examples of main diseases to which the compounds of this invention are applicable include potato late blight (*Phytophthora infestans*), tomato late blight (*Phytophthora infestans*), tobacco black shank (*Phytophthora parasitica* var. nicotianae), strawberry leather rot (*Phytophthora cartorum*), Phytophthora rot of adzuki bean, vine downy mildew (*Plasmopara viticola*), cucumber downy mildew (*Pseudoperonospora cubensis*), hop downy mildew (*Pseudoperonospora humuli*), downy mildew of garland chrysnathemum (*Peronospora chrysanthemi*) or seedling damping off of various crops caused by fungi of the genus Aphanomyces and Pythium.

The method of applying the compounds of this invention is, for example, seed dressing, foliar application, soil drench, or soil incorporation. They exhibit sufficient efficacies by any methods of application which those skilled in the art normally use. The rate of application and the concentration of application vary depending upon a crop to which they are applied, the type of a disease to be controlled, the type of a formulation, the method of application and various environmental conditions. In spraying, the suitable rate of application is 5 to 200 g, desirably 10 to 100 g, per are, and the suitable concentration of spraying is 20 to 1,000 ppm, and desirably 50 to 500 ppm.

The herbicide and the fungicide of this invention can be used in admixture with compounds having other biological activities, for example agricultural chemicals such as another fungicide, an insecticide, another herbicide or a plant growth regulator, a soil conditioner or a fertilizer material. Alternatively, mixed formulations may be prepared from both.

The compounds of this invention may be directly applied, but preferably in the form of a composition in which the active ingredient is mixed with a carrier comprising a solid or liquid diluent. The carrier, as used herein, denotes a synthetic or natural inorganic or organic material which aids in the arrival of the active ingredient at a locus to be treated and facilitates storing, transporting and handling of the active compound.

Examples of suitable solid carriers include clays such as montmorillonite and kaolinite, inorganic materials such as diatomaceous earth, terra alba, talc, vermiculite, gypsum, calcium carbonate, silica gel and ammonium sulfate, organic substances of the vegetable origin such as soybean meal, saw dust and wheat flour; and urea.

Examples of suitable liquid carriers include aromatic hydrocarbons such as toluene, xylene and cumene; paraffinic hydrocarbons such as kerosene and mineral oils; halogenated hydrocarbons such as carbon tetrachloride, chloroform and dichloroethane; ketones such as acetone and methyl ethyl ketone; ethers such as dioxane and tetrahydrofuran; alcohols such as methanol, propanol and ethylene glycol; dimethyl formamide; dimethyl sulfoxide; and water.

To increase the efficacy of the compounds of this invention, various auxiliary agents may be used singly or in combination according to varous purposes such as emulsification, dispersion, spreading, wetting, binding and stabilization by taking the type of the formulation and the situation of application into consideration. Examples of such adjuvants include water-soluble bases such as lignin sulfonates; nonionic surface-active agents such as alkylbenzene sulfonates and alkylsulfate esters; lubricants such as calcium stearate and waxes; stabilizers such as isopropyl hydrogen phosphate; methyl cellulose; carboxymethyl cellulose; casein; and gum arabic.

The amount of the active ingredient in the composition of the compound of this invention is usually 0.5 to 20% by weight for a dust, 10 to 90% by weight for a wettable powder, 0.1 to 20% by weight for granules, 5 to 50% by weight for an emulsifiable concentrate, and 10 to 90% by weight for a flowable composition.

Typical examples of the substituted propargyloxyacetonitrile derivatives of this invention represented by the general formula (I) are shown in Table 1 below.

TABLE 1

$$\underset{R_n}{\phantom{xx}}\text{-C}_6\text{H}_4\text{-CONHCH}(\text{CN})\text{-OCH}(R^1)\text{-C}\equiv\text{C-}R^2 \quad (I)$$

| Compound No. | $R_n$–C₆H₄– | $R^1$ | $R^2$ | Property (m.p., °C.) | NMR (100 MHz, δ) |
|---|---|---|---|---|---|
| 1 | C₆H₅ | H | CH₃ | 84–85.5 | $\delta_{TMS}^{CDCl_3\text{-}DMSO\text{-}d_6}$ (ppm): 1.82 (3H, t), 4.30 (2H, q), 6.40 (1H, d), 7.2–8.1 (5H, m), 9.37 (1H, d) |
| 2 | 2-Cl-C₆H₄ | H | CH₃ | 71–72 | $\delta_{TMS}^{CDCl_3}$ (ppm): 1.80 (3H, t), 4.37 (2H, q), 6.42 (1H, d), 7.1–7.9 (5H, m) |
| 3 | 3-Cl-C₆H₄ | H | CH₃ | 86–87 | $\delta_{TMS}^{CDCl_3}$ (ppm): 1.85 (3H, t), 4.32 (2H, q), 6.40 (1H, d), 7.2–7.9 (5H, m) |
| 4 | 3,4-Cl₂-C₆H₃ | H | CH₃ | 93–94 | $\delta_{TMS}^{CDCl_3\text{-}DMSO\text{-}d_6}$ (ppm): 1.80 (3H, t), 4.35 (2H, q), 6.38 (1H, d), 7.3–8.2 (3H, m), 9.92 (1H, d) |
| 5 | 3,5-Cl₂-C₆H₃ | H | CH₃ | 124–128 | $\delta_{TMS}^{CDCl_3\text{-}DMSO\text{-}d_6}$ (ppm): 1.85 (3H, t), 4.30 (2H, q), 6.38 (1H, d), 7.3–8.0 (3H, m), 9.50 (1H, d) |
| 6 | 2-F-C₆H₄ | H | CH₃ | 54.5–55.5 | $\delta_{TMS}^{CDCl_3}$ (ppm): 1.87 (3H, t), 4.38 (2H, q), 6.48 (1H, d), 7.0–8.2 (5H, m) |
| 7 | 3-F-C₆H₄ | H | CH₃ | 54.5–55 | $\delta_{TMS}^{CDCl_3\text{-}DMSO\text{-}d_6}$ (ppm): 1.85 (3H, t), 4.35 (2H, q), 6.45 (1H, d), 7.0–7.9 (4H, m), 9.67 (1H, d) |
| 8 | 4-F-C₆H₄ | H | CH₃ | 63.5–64.5 | $\delta_{TMS}^{CDCl_3}$ (ppm): 1.88 (3H, t), 4.50 (2H, q), 6.42 (1H, d), 6.9–8.0 (5H, m) |
| 9 | 2-Br-C₆H₄ | H | CH₃ | 62–63 | $\delta_{TMS}^{CDCl_3}$ (ppm): 1.88 (3H, t), 4.38 (2H, q), 6.42 (1H, d), 7.2–8.1 (5H, m) |

TABLE 1-continued

Structure (I):
$R_n$-C6H4-CONHCH(CN)-OCH(R^1)-C≡C-R^2

| Compound No. | Aryl ($R_n$-phenyl) | $R^1$ | $R^2$ | Property (m.p., °C.) | NMR (100 MHz, δ) |
|---|---|---|---|---|---|
| 10 | 2-CH₃-C₆H₄ | H | CH₃ | 63.5–64.5 | $\delta^{CDCl_3}_{TMS}$ (ppm): 1.83 (3H, t), 2.37 (3H, s), 4.40 (2H, q), 6.42 (1H, d), 7.2–7.8 (5H, m) |
| 11 | 4-CH₃-C₆H₄ | H | CH₃ | 105–106 | $\delta^{CDCl_3}_{TMS}$ (ppm): 1.85 (3H, t), 2.42 (3H, s), 4.38 (2H, q), 6.43 (1H, d), 7.1–7.9 (5H, m) |
| 12 | 3,5-(CH₃)₂-C₆H₃ | H | CH₃ | 117–119 | $\delta^{CDCl_3}_{TMS}$ (ppm): 1.82 (3H, t), 2.38 (6H, s), 4.31 (2H, q), 6.43 (1H, d), 7.1–7.5 (4H, m) |
| 13 | 3-CH₃O-C₆H₄ | H | CH₃ | 60.5–62 | $\delta^{CDCl_3}_{TMS}$ (ppm): 1.82 (3H, t), 3.82 (3H, s), 4.35 (2H, q), 6.45 (1H, d), 6.9–7.7 (5H, m) |
| 14 | 4-CH₃O-C₆H₄ | H | CH₃ | 73–74 | $\delta^{CDCl_3}_{TMS}$ (ppm): 1.82 (3H, t), 3.87 (3H, s), 4.32 (2H, q), 6.37 (1H, d), 6.8–8.0 (5H, m) |
| 15 | 3,5-(CH₃O)₂-C₆H₃ | H | CH₃ | 110–111 | $\delta^{CDCl_3}_{TMS}$ (ppm): 1.85 (3H, t), 3.90 (6H, s), 4.31 (2H, q), 6.43 (1H, d), 6.8–7.6 (4H, m) |
| 16 | 3,4-methylenedioxyphenyl | H | CH₃ | 111–113 | $\delta^{CDCl_3}_{TMS}$ (ppm): 1.85 (3H, t), 4.34 (2H, q), 6.04 (2H, s), 6.42 (1H, d), 6.8–7.7 (4H, m) |
| 17 | 3-CF₃-C₆H₄ | H | CH₃ | 83–83.5 | $\delta^{CDCl_3}_{TMS}$ (ppm): 1.87 (3H, t), 4.37 (2H, q), 6.48 (1H, d), 7.1–8.2 (5H, m) |
| 18 | 4-CF₃-C₆H₄ | H | CH₃ | 94–96 | $\delta^{CDCl_3}_{TMS}$ (ppm): 1.84 (3H, t), 4.38 (2H, q), 6.45 (1H, d), 7.3–8.1 (5H, m) |

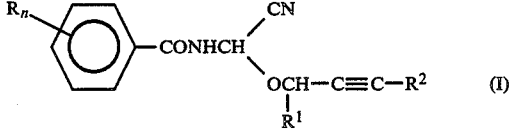

TABLE 1-continued

Structure (I):
Ar-CONHCH(CN)-OCH(R¹)-C≡C-R²   where Ar = R$_n$-phenyl

| Compound No. | R$_n$-phenyl | R¹ | R² | Property (m.p., °C.) | NMR (100 MHz, δ) |
|---|---|---|---|---|---|
| 19 | o-O$_2$N-C$_6$H$_4$- | H | CH$_3$ | 90–92 | $\delta^{CDCl_3}_{TMS}$ (ppm): 1.82 (3H, t), 4.40 (2H, q), 6.46 (1H, d), 7.5–8.8 (5H, m) |
| 20 | o-NC-C$_6$H$_4$- | H | CH$_3$ | 125–129 | $\delta^{CDCl_3}_{TMS}$ (ppm): 1.85 (3H, d), 4.37 (2H, q), 6.42 (1H, d), 7.5–8.3 (5H, m) |
| 21 | C$_6$H$_5$- | H | I | 111–113 | $\delta^{CDCl_3-DMSO-d_6}_{TMS}$ (ppm): 4.48 (2H, s), 6.37 (1H, d), 7.4~8.2 (5H, m), 9.70 (1H, d) |
| 22 | o-Cl-C$_6$H$_4$- | H | I | 91–93 | $\delta^{CDCl_3-DMSO-d_6}_{TMS}$ (ppm): 4.52 (2H, s), 6.38 (1H, d), 7.2–8.1 (4H, m), 9.10 (1H, d) |
| 23 | p-Cl-C$_6$H$_4$- | H | I | 88–90 | $\delta^{CDCl_3-DMSO-d_6}_{TMS}$ (ppm): 4.52 (2H, s), 6.40 (1H, d), 7.3–8.1 (4H, m), 9.10 (1H, d) |
| 24 | 2,3-Cl$_2$-C$_6$H$_3$- | H | I | 102–104 | $\delta^{CDCl_3}_{TMS}$ (ppm): 4.54 (2H, s), 6.43 (1H, d), 7.4–8.0 (4H, m) |
| 25 | 3,5-Cl$_2$-C$_6$H$_3$- | H | I | 128–130 | $\delta^{CDCl_3-DMSO-d_6}_{TMS}$ (ppm): 4.50 (2H, s), 6.30 (1H, d), 7.2–8.1 (3H, m), 9.25 (1H, d) |
| 26 | o-F-C$_6$H$_4$- | H | I | 114–115 | $\delta^{CDCl_3}_{TMS}$ (ppm): 4.52 (2H, s), 6.42 (1H, dd), 6.9–8.3 (5H, m) |
| 27 | m-F-C$_6$H$_4$- | H | I | 99–100 | $\delta^{CDCl_3-DMSO-d_6}_{TMS}$ (ppm): 4.50 (2H, s), 6.32 (1H, d), 7.0–7.9 (4H, m), 9.95 (1H, d) |
| 28 | p-F-C$_6$H$_4$- | H | I | 118–119 | $\delta^{CDCl_3-DMSO-d_6}_{TMS}$ (ppm): 4.50 (2H, s), 6.38 (1H, d), 6.9–8.1 (4H, m), 9.62 (1H, d) |

TABLE 1-continued $$\underset{R_n}{\text{R}_n}\!\!\!\!\!\!\!\!\!\!\!\!\!\!\!\!\!\!\!\!\!\!\!\!\!\!\!\!\!\!\!\!-\text{CONHCH}\!\!\begin{array}{c}\text{CN}\\|\\\text{OCH}-\text{C}\!\equiv\!\text{C}-\text{R}^2\\|\\\text{R}^1\end{array}\quad\text{(I)}$$

| Compound No. | $R_n$-phenyl | $R^1$ | $R^2$ | Property (m.p., °C.) | NMR (100 MHz, δ) |
|---|---|---|---|---|---|
| 29 | 2-Br-phenyl | H | I | 108–110 | $\delta_{TMS}^{CDCl_3\text{-}DMSO\text{-}d_6}$ (ppm): 6.54 (2H, s), 6.42 (1H, d), 7.2–8.3 (4H, m), 9.38 (1H, d) |
| 30 | 2-CH$_3$-phenyl | H | I | 87–88 | $\delta_{TMS}^{CDCl_3\text{-}DMSO\text{-}d_6}$ (ppm): 2.36 (3H, s), 4.50 (2H, s), 6.38 (1H, d), 7.1–7.9 (4H, d), 8.70 (1H, d) |
| 31 | 3-CH$_3$-phenyl | H | I | 104–106 | $\delta_{TMS}^{CDCl_3\text{-}DMSO\text{-}d_6}$ (ppm): 2.40 (3H, s), 4.50 (2H, s), 6.38 (1H, d), 7.0–8.0 (4H, m), 8.80 (1H, d) |
| 32 | 3,5-(CH$_3$)$_2$-phenyl | H | I | 113–114 | $\delta_{TMS}^{CDCl_3}$ (ppm): 2.37 (6H, s), 4.52 (2H, s), 6.40 (1H, d), 7.1–7.6 (4H, m) |
| 33 | 3-CH$_3$O-phenyl | H | I | 82–84 | $\delta_{TMS}^{CDCl_3}$ (ppm): 3.87 (3H, s), 4.52 (2H, s), 6.38 (1H, d), 6.9–7.9 (5H, m) |
| 34 | 4-CH$_3$O-phenyl | H | I | 96–98 | $\delta_{TMS}^{CDCl_3}$ (ppm): 3.88 (3H, s), 4.46 (2H, s), 6.32 (1H, d), 6.7–8.0 (4H, m), 8.25 (1H, d) |
| 35 | 3,5-(CH$_3$O)$_2$-phenyl | H | I | 118–119 | $\delta_{TMS}^{CDCl_3\text{-}DMSO\text{-}d_6}$ (ppm): 3.82 (6H, s), 4.48 (2H, s), 6.37 (1H, d), 6.5–7.3 (3H, m), 9.90 (1H, d) |
| 36 | 3,4-methylenedioxy-phenyl | H | I | 150–152 | $\delta_{TMS}^{CDCl_3\text{-}DMSO\text{-}d_6}$ (ppm): 4.52 (2H, s), 6.05 (2H, s), 6.38 (1H, d), 6.7–7.7 (3H, m), 9.48 (1H, d) |
| 37 | 2-CF$_3$-phenyl | H | I | 67–69 | $\delta_{TMS}^{CDCl_3}$ (ppm): 4.57 (2H, s), 6.42 (1H, d), 7.4–8.2 (5H, m) |

TABLE 1-continued $$R_n\text{-}C_6H_4\text{-}CONHCH(CN)\text{-}OCH(R^1)\text{-}C\equiv C\text{-}R^2 \quad (I)$$

| Compound No. | $R_n$-C$_6$H$_4$- | $R^1$ | $R^2$ | Property (m.p., °C.) | NMR (100 MHz, δ) |
|---|---|---|---|---|---|
| 38 | 3-O$_2$N-C$_6$H$_4$- | H | I | 125–127 | $\delta_{TMS}^{CDCl_3\text{-}DMSO\text{-}d_6}$ (ppm): 4.53 (2H, s), 6.34 (1H, d), 7.5–9.0 (4H, m), 10.40 (1H, d) |
| 39 | 3-NC-C$_6$H$_4$- | H | I | 134–135 | $\delta_{TMS}^{CDCl_3\text{-}DMSO\text{-}d_6}$ (ppm): 4.50 (2H, s), 6.38 (1H, d), 7.3–8.5 (4H, m), 10.10 (1H, d) |
| 40 | C$_6$H$_5$- | H | Br | 99–100 | $\delta_{TMS}^{CDCl_3\text{-}DMSO\text{-}d_6}$ (ppm): 4.37 (2H, s), 6.37 (1H, d), 7.2–8.1 (5H, m), 9.52 (1H, d) |
| 41 | 3-Cl-C$_6$H$_4$- | H | Br | 86–88 | $\delta_{TMS}^{CDCl_3}$ (ppm): 4.40 (2H, s), 6.38 (1H, d), 7.2–7.9 (5H, m) |
| 42 | 4-Cl-C$_6$H$_4$- | H | Br | 81–83 | $\delta_{TMS}^{CDCl_3}$ (ppm): 4.40 (2H, s), 6.38 (1H, d), 7.2–7.9 (5H, m) |
| 43 | 3,5-Cl$_2$-C$_6$H$_3$- | H | Br | 128–130 | $\delta_{TMS}^{CDCl_3\text{-}DMSO\text{-}d_6}$ (ppm): 4.37 (2H, s), 6.30 (1H, d), 7.4–8.0 (3H, m), 10.06 (1H, d) |
| 44 | 3-H$_3$C-C$_6$H$_4$- | H | Br | 85–86 | $\delta_{TMS}^{CDCl_3}$ (ppm): 2.38 (3H, s), 4.36 (2H, s), 6.37 (1H, d), 7.1–7.9 (5H, m) |
| 45 | 4-H$_3$C-C$_6$H$_4$- | H | Br | 115–117 | $\delta_{TMS}^{CDCl_3}$ (ppm): 2.41 (3H, s), 4.38 (2H, s), 6.34 (1H, d), 7.0–7.8 (5H, m) |
| 46 | 3-F-C$_6$H$_4$- | H | Br | 98–100 | $\delta_{TMS}^{CDCl_3}$ (ppm): 4.42 (2H, s), 6.43 (1H, dd), 7.0–8.3 (5H, m) |

TABLE 1-continued $$\underset{R_n}{\phantom{X}}\text{—}\underset{\text{CONHCH}}{\text{C}_6H_4}\text{—}\underset{\overset{|}{R^1}}{\text{OCH}}\text{—C}≡\text{C—R}^2 \qquad (I)$$

with CN on the CH carbon

| Compound No. | $R_n$-phenyl | $R^1$ | $R^2$ | Property (m.p., °C.) | NMR (100 MHz, δ) |
|---|---|---|---|---|---|
| 47 | F (o-F) | H | Br | 77–78 | $\delta_{TMS}^{CDCl_3}$ (ppm): 4.42 (2H, s), 6.41 (1H, d), 7.0–7.8 (4H, m), 8.03 (1H, d) |
| 48 | 3,4-Cl$_2$ | H | Br | 107–108 | $\delta_{TMS}^{CDCl_3\text{-}DMSO\text{-}d_6}$ (ppm): 4.38 (2H, s), 6.33 (1H, d), 7.3–8.2 (3H, m), 9.94 (1H, d) |
| 49 | 3,5-(CH$_3$)$_2$ | H | Br | 112–114 | $\delta_{TMS}^{CDCl_3}$ (ppm): 2.38 (6H, s), 4.40 (2H, s), 6.40 (1H, d), 7.1–7.5 (4H, m) |
| 50 | 4-Cl | H | CH$_2$Cl | 88–89 | $\delta_{TMS}^{CDCl_3}$ (ppm): 4.10 (2H, t), 4.42 (2H, t), 6.36 (1H, d), 7.1–8.0 (5H, m) |
| 51 | 2,4-Cl$_2$ | H | CH$_2$Cl | 98–99 | $\delta_{TMS}^{CDCl_3}$ (ppm): 4.15 (2H, t), 4.46 (2H, t), 6.40 (1H, d), 7.4–8.0 (4H, m) |
| 52 | 2,4-Cl$_2$ | H | C$_2$H$_5$ | 100–101 | $\delta_{TMS}^{CDCl_3}$ (ppm): 1.12 (3H, t), 2.20 (2H, m), 4.32 (2H, t), 6.41 (1H, d), 7.3–8.0 (4H, m) |
| 53 | 2,4-Cl$_2$ | H | n-C$_3$H$_7$ | 85–86 | $\delta_{TMS}^{CDCl_3}$ (ppm): 0.92 (3H, m), 1.54 (2H, m), 2.18 (2H, m), 4.36 (2H, t), 6.40 (1H, d), 7.3–7.9 (4H, m) |
| 54 | 2,4-Cl$_2$ | H | n-C$_4$H$_9$ | 89–90 | $\delta_{TMS}^{CDCl_3}$ (ppm): 0.65–1.65 (7H, m), 2.32 (2H, m), 4.30 (2H, t), 6.32 (1H, d), 7.3–7.7 (4H, m) |

TABLE 1-continued $$R_n\text{-Ph-CONHCH(CN)-OCH(R}^1\text{)-C}\equiv\text{C-R}^2 \quad (I)$$

| Compound No. | $R_n$-Ph | $R^1$ | $R^2$ | Property (m.p., °C.) | NMR (100 MHz, δ) |
|---|---|---|---|---|---|
| 55 | 2,4-diCl-Ph | CH₃ | H | 118–120 | $\delta^{CDCl_3}_{TMS}$ (ppm): 1.48 (3H, dd), 2.60 (1H, t), 4.58 (1H, m), 6.47 (1H, dd), 7.4–8.2 (4H, m) |
| 56 | 4-F-Ph | H | Br | 85–87 | $\delta^{CDCl_3}_{TMS}$ (ppm): 4.40 (2H, s), 6.36 (1H, d), 6.9–8.1 (5H, m) |
| 57 | 3-Br-Ph | H | Br | 90–92 | $\delta^{CDCl_3}_{TMS}$ (ppm): 4.40 (2H, s), 6.38 (1H, d), 7.1–8.0 (5H, m) |
| 58 | 2-CH₃O-Ph | H | Br | 75–77 | $\delta^{CDCl_3}_{TMS}$ (ppm): 3.82 (3H, s), 4.40 (2H, s), 6.38 (1H, d), 6.9–7.5 (4H, m), 7.95 (1H, d) |
| 59 | 4-CH₃O-Ph | H | Br | 115–117 | $\delta^{CDCl_3\text{-}DMSO\text{-}d_6}_{TMS}$ (ppm): 3.86 (3H, s), 4.38 (2H, s), 6.36 (1H, d), 6.8–7.1 (2H, m), 7.8–8.1 (2H, m), 9.33 (1H, d) |
| 60 | 3,5-diCH₃O-Ph | H | Br | 106–107 | $\delta^{CDCl_3}_{TMS}$ (ppm): 3.80 (6H, s), 4.38 (2H, s), 6.40 (1H, d), 6.6 (1H, m), 6.9 (2H, m), 7.54 (1H, d) |
| 61 | 3,4-methylenedioxy-Ph | H | Br | 138–140 | $\delta^{CDCl_3\text{-}DMSO\text{-}d_6}_{TMS}$ (ppm): 4.40 (2H, s), 6.02 (2H, s), 6.37 (1H, d), 6.8 (1H, m), 7.5 (2H, m), 9.58 (1H, d) |
| 62 | 3-CF₃-Ph | H | Br | 86–90 | $\delta^{CDCl_3}_{TMS}$ (ppm): 4.42 (2H, s), 6.40 (1H, d), 7.3–8.2 (5H, m) |
| 63 | 4-CF₃-Ph | H | Br | 109–111 | $\delta^{CDCl_3}_{TMS}$ (ppm): 4.45 (2H, s), 6.38 (1H, d), 7.5–8.1 (5H, m) |

TABLE 1-continued

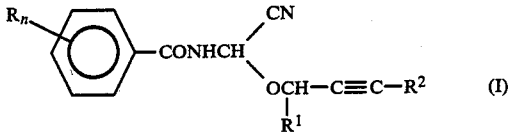

| Compound No. | $R_n$ | $R^1$ | $R^2$ | Property (m.p., °C.) | NMR (100 MHz, δ) |
|---|---|---|---|---|---|
| 64 | NO$_2$ (3-) | H | Br | 131–132 | $\delta^{CDCl_3-DMSO-d_6}_{TMS}$ (ppm): 4.42 (2H, s), 6.37 (1H, d), 7.5–9.0 (4H, m), 10.35 (1H, d) |
| 65 | NC (3-) | H | Br | 120–124 | $\delta^{CDCl_3-DMSO-d_6}_{TMS}$ (ppm): 4.40 (2H, s), 6.34 (1H, d), 7.4–8.5 (4H, m), 10.18 (1H, d) |
| 66 | 3,4-(CH$_3$)$_2$ | H | Br | 81–83 | $\delta^{CDCl_3}_{TMS}$ (ppm): 2.28 (6H, s), 4.35 (2H, s), 6.40 (1H, d), 7.1–7.9 (4H, m) |
| 67 | Cl (3-) | H | Cl | 67–68 | $\delta^{CDCl_3-DMSO-d_6}_{TMS}$ (ppm): 4.40 (2H, s), 6.31 (1H, d), 7.3–8.1 (4H, m), 10.10 (1H, d) |
| 68 | 3,5-Cl$_2$ | H | Cl | 123–125 | $\delta^{CDCl_3-DMSO-d_6}_{TMS}$ (ppm): 4.38 (2H, s), 6.28 (1H, d), 7.5–8.1 (3H, m), 10.23 (1H, d) |
| 69 | 3,5-(CH$_3$)$_2$ | H | Cl | 90–91 | $\delta^{CDCl_3-DMSO-d_6}_{TMS}$ (ppm): 2.43 (6H, s), 4.38 (2H, s), 6.30 (1H, d), 7.1–7.5 (3H, m), 10.15 (1H, d) |
| 70 | H | CH$_3$ | H | 95–97 | $\delta^{CDCl_3}_{TMS}$ (ppm): 1.47 (3H, dd), 2.60 (1H, t), 4.55 (1H, m), 6.54 (1H, dd), 7.2–8.0 (6H, m) |
| 71 | Cl (3-) | CH$_3$ | H | 72–73 | $\delta^{CDCl_3}_{TMS}$ (ppm): 1.52 (3H, dd), 2.62 (1H, t), 4.58 (1H, m), 6.50 (1H, dd), 7.0–8.0 (5H, m) |
| 72 | Cl (4-) | CH$_3$ | H | 68–69 | $\delta^{CDCl_3}_{TMS}$ (ppm): 1.62 (3H, dd), 2.58 (1H, t), 4.53 (1H, m), 6.48 (1H, dd), 7.1–8.0 (5H, m) |

TABLE 1-continued $$R_n-\text{C}_6\text{H}_4-\text{CONHCH}(\text{CN})-\text{OCH}(R^1)-\text{C}\equiv\text{C}-R^2 \quad (I)$$

| Compound No. | $R_n$-phenyl | $R^1$ | $R^2$ | Property (m.p., °C.) | NMR (100 MHz, δ) |
|---|---|---|---|---|---|
| 73 | 2-F | $CH_3$ | H | 70–71 | $\delta_{TMS}^{CDCl_3}$ (ppm): 1.47 (3H, dd), 2.64 (1H, t), 4.58 (1H, m), 6.55 (1H, m), 6.9–8.3 (5H, m) |
| 74 | 3-F | $CH_3$ | H | 64–65 | $\delta_{TMS}^{CDCl_3}$ (ppm): 1.58 (3H, dd), 2.70 (1H, t), 4.58 (1H, m), 6.53 (1H, dd), 7.1–8.0 (5H, m) |
| 75 | 4-F | $CH_3$ | H | 79–81 | $\delta_{TMS}^{CDCl_3}$ (ppm): 1.48 (3H, dd), 2.62 (1H, t), 4.58 (1H, m), 6.49 (1H, dd), 6.9–8.1 (5H, m) |
| 76 | 2-Br | $CH_3$ | H | 79–82 | $\delta_{TMS}^{CDCl_3}$ (ppm): 1.48 (3H, dd), 2.59 (1H, t), 4.52 (1H, m), 6.47 (1H, dd), 7.1–8.2 (5H, m) |
| 77 | 3-$CH_3$ | $CH_3$ | H | 70–71 | $\delta_{TMS}^{CDCl_3}$ (ppm): 1.48 (3H, dd), 2.37 (3H, s), 2.60 (1H, t,) 4.56 (1H, m), 6.52 (1H, dd), 7.2–7.8 (5H, m) |
| 78 | 4-$CH_3$ | $CH_3$ | H | 100–101 | $\delta_{TMS}^{CDCl_3}$ (ppm): 1.48 (3H, dd), 2.37 (3H, s), 2.59 (1H, t), 4.54 (1H, m), 6.45 (1H, dd), 6.9–8.0 (5H, m) |
| 79 | 3,5-di-$CH_3$ | $CH_3$ | H | 83–85 | $\delta_{TMS}^{CDCl_3}$ (ppm): 1.54 (3H, dd), 2.28 (6H, s), 2.62 (1H, t), 4.54 (1H, m), 6.50 (1H, dd), 7.1–7.7 (4H, m) |
| 80 | 3-$CH_3O$ | $CH_3$ | H | 84–85 | $\delta_{TMS}^{CDCl_3}$ (ppm): 1.47 (3H, dd), 2.58 (1H, t), 3.80 (3H, s), 4.54 (1H, m), 6.50 (1H, dd), 6.9–8.0 (5H, m) |
| 81 | 4-$CH_3O$ | $CH_3$ | H | 86–87 | $\delta_{TMS}^{CDCl_3}$ (ppm): 1.50 (3H, dd), 2.60 (1H, t), 3.82 (3H, s), 4.60 (1H, m), 6.45 (1H, dd), 6.8–8.0 (5H, m) |

TABLE 1-continued $$R_n\text{-C}_6H_4\text{-CONHCH}(CN)\text{-OCH}(R^1)\text{-C}{\equiv}C\text{-}R^2 \quad (I)$$

| Compound No. | $R_n$-phenyl | $R^1$ | $R^2$ | Property (m.p., °C.) | NMR (100 MHz, δ) |
|---|---|---|---|---|---|
| 82 | 2,4-(CH$_3$O)$_2$ | CH$_3$ | H | 126–128 | $\delta_{TMS}^{CDCl_3}$ (ppm): 1.49 (3H, dd), 2.52 (1H, t), 3.85 (6H, s), 4.60 (1H, m), 6.4–7.2 (4H, m) |
| 83 | 3,4-methylenedioxy | CH$_3$ | H | 107–108 | $\delta_{TMS}^{CDCl_3\text{-}DMSO\text{-}d_6}$ (ppm): 1.43 (3H, dd), 2.68 (1H, t), 4.50 (1H, m), 6.02 (2H, s), 6.38 (1H, dd), 6.6–7.7 (3H, m), 9.45 (1H, d) |
| 84 | 3-CF$_3$ | CH$_3$ | H | 51–52 | $\delta_{TMS}^{CDCl_3}$ (ppm): 1.46 (3H, dd), 2.55 (1H, t), 4.54 (1H, m), 6.50 (1H, dd), 7.3–8.6 (5H, m) |
| 85 | 3-NO$_2$ | CH$_3$ | H | 76–77 | $\delta_{TMS}^{CDCl_3}$ (ppm): 1.47 (3H, dd), 2.62 (1H, t), 4.62 (1H, m), 6.57 (1H, dd), 7.5–9.0 (5H, m) |
| 86 | 3-NC | CH$_3$ | H | 82–84 | $\delta_{TMS}^{CDCl_3}$ (ppm): 1.35 (3H, dd), 2.63 (1H, t), 4.58 (1H, m), 6.48 (1H, dd), 7.4–8.7 (5H, m) |
| 87 | 3,4-(CH$_3$)$_2$ | CH$_3$ | H | 84–85 | $\delta_{TMS}^{CDCl_3}$ (ppm): 1.44 (3H, dd), 2.28 (6H, s), 2.57 (1H, t), 4.50 (1H, m), 6.52 (1H, dd), 7.0–8.0 (4H, m) |
| 88 | 3-F | C$_2$H$_5$ | H | 74–75 | $\delta_{TMS}^{CDCl_3}$ (ppm): 1.06 (3H, q), 1.78 (2H, m), 2.62 (1H, t), 4.41 (1H, m), 6.53 (1H, d), 7.0–8.2 (5H, m) |
| 89 | 3-Cl | C$_2$H$_5$ | H | 61–62 | $\delta_{TMS}^{CDCl_3}$ (ppm): 1.07 (3H, q), 1.80 (2H, m), 2.58 (1H, t), 4.37 (1H, m), 6.45 (1H, d), 7.1–8.3 (5H, m) |
| 90 | 3,4-Cl$_2$ | C$_2$H$_5$ | H | 128–129 | $\delta_{TMS}^{CDCl_3\text{-}DMSO\text{-}d_6}$ (ppm): 0.98 (3H, q), 1.72 (2H, m), 2.80 (1H, t), 4.37 (1H, m), 6.32 (1H, d), 7.4–8.1 (3H, m), 10.12 (1H, d) |

TABLE 1-continued

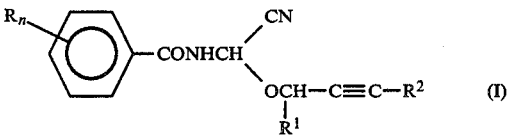

| Compound No. | Rn-phenyl | R¹ | R² | Property (m.p., °C.) | NMR (100 MHz, δ) |
|---|---|---|---|---|---|
| 91 | CF₃ (phenyl-phenyl) | C₂H₅ | H | 50–52 | $\delta_{TMS}^{CDCl_3}$ (ppm): 1.06 (3H, q), 1.78 (2H, m), 2.62 (1H, t), 4.38 (1H, m), 6.52 (1H, d), 7.3–8.5 (5H, m) |
| 92 | CH₃O (phenyl-phenyl) | C₂H₅ | H | 62–64 | $\delta_{TMS}^{CDCl_3}$ (ppm): 1.02 (3H, q), 1.78 (2H, m), 2.58 (1H, t), 3.85 (3H, s), 4.38 (1H, m), 6.47 (1H, d), 6.9–7.5 (4H, m), 8.20 (1H, d) |
| 93 | CH₃-/CH₃- phenyl | C₂H₅ | H | 82 | $\delta_{TMS}^{CDCl_3}$ (ppm): 1.05 (3H, q), 1.78 (2H, m), 2.33 (6H, s), 2.57 (1H, t), 4.30 (1H, m), 6.52 (1H, d), 7.0–7.9 (4H, m) |

The process of this invention for producing the compounds of this invention will be specifically illustrated by Synthesis Examples.

SYNTHESIS EXAMPLE 1

Synthesis of alpha-benzoylamino-(2-butynyloxy)-acetonitrile (Compound No. 1):

Benzoylaminoacetonitrile was synthesized in a conventional manner from benzoyl chloride and aminoacetonitrile. Bromine (40 g) was added at a time to a solution of 4.0 g of the benzoylaminoacetonitrile in 200 ml of ethyl acetate at room temperature. When the color of bromine in the reaction solution disappeared, the reaction solution was cooled to 0° to 5° C. 2-Butyn-1-ol (2.1 g) and 5.6 g of triethylamine were dissolved in 10 ml of ethyl acetate, and the solution was added dropwise to the ethyl acetate solution previously cooled. After the addition, the reaction was continued for 30 minutes at room temperature. Triethylamine hydrobromide was separated by filtration, and the filtrate was distilled under reduced pressure to evaporate the solvent. The residue was purified by silica gel column chromatography. By elution with hexane-ethyl acetate, 3.8 g of alpha-benzoylamino-(2-butynyloxy)acetonitrile was obtained as a solid. The yield was 65.5%, and the melting point of the product was 84° to 85.5° C.

NMR $\delta_{TMS}^{CDCl_3-DMSO-d_6}$ (ppm):
1.82 (3H, t), 4.30 (2H, q), 6.40 (1H, d), 7.2–8.1 (5H, m), 9.37 (1H, d).

The starting acylaminonitrile can be easily produced by reacting an acyl halide with aminoacetonitrile in a conventional manner, for example by the following procedure.

For example, a 10% aqueous solution of sodium hydroxide is cooled in ice water, and with stirring, sulfuric acid and aminoacetonitrile are added to form a solution. A toluene solution of an acid halide is added drop-wise under ice cooling, and after the addition, the mixture is stirred at the same temperature. The precipitated crystals were collected by suction filtration, washed first with toluene and then with water, and then dried.

SYNTHESIS EXAMPLE 2

Synthesis of alpha-(2-butynyloxy)-3,5-dichlorobenzoylaminoacetonitrile (Compound No. 5):

Bromine (2.8 g) was added at a time to a solution of 4.0 g of 3,5-dichlorobenzoyl aminoacetonitrile in 100 ml of ethyl acetate at room temperature. The mixture was stirred until the color of bromine in the reaction solution disappeared. The reaction solution was then cooled to 0° to 5° C. A mixture of 1.5 g of 2-butyn-1-ol, 3.5 g of triethylamine and 30 ml of tetrahydrofuran was cooled to 0° to 5° C. on an ice bath, and with stirring, the ethyl acetate solution of the bromine compound prepared above was added dropwise. After the addition, the reaction was continued for 30 minutes under cooling. Water (100 ml) was added to dissolve the precipitated triethylamine hydrobromide. The oil layer was separated, washed with water, and dried. The solvent was then distilled off under reduced pressure. The residual solid was suspended in ethyl ether, filtered, washed and dried to give 4.2 g of the desired alpha-(2-butynyloxy)-3,5-dichlorobenzoylaminoacetonitrile as a white solid. The yield was 79.9%, and the melting point of the product was 124° to 128° C.

NMR $\delta_{TMS}^{CDCl_3-DMSO-d_6}$ (ppm):
1.85 (3H, t), 4.30 (2H, q), 6.38 (1H, d), 7.3–8.0 (3H, m), 9.50 (1H, d).

SYNTHESIS EXAMPLE 3

Synthesis of alpha-(3,5-dichlorobenzoylamino)-(3-iodopropargyloxy)acetonitrile (Compound No. 25):

Bromine (2.8 g) was added at a time to a solution of 4.0 g of 3,5-dichlorobenzoylaminoacetonitrile in 100 ml of ethyl acetate at room temperature. The mixture was stirred until the color of bromine in the reaction solution disappeared. Then, the reaction solution was cooled to 0° to 5° C. A mixture of 3.8 g of 3-iodopropargyl alcohol, 3.5 g of triethylamine and 30 ml of tetrahydrofuran was cooled to 0° to 5° C. over an ice bath. The ethyl acetate solution of the bromine compound prepared above was added dropwise to this mixture with stirring. After the addition, the reaction was continued for 30 minutes under ice cooling. Water (100 ml) was added to dissolve the precipitated triethylamine hydrobromide. The oily layer was separated, washed with water and dried. The solvent was then evaporated under reduced pressure. When ethyl ether was added to the residue, 5.3 g of the desired alpha-(3,5-dichlorobenzoylamino)-(3-iodopropargyloxy)acetonitrile was obtained as a white solid. The yield was 71.1%, and the melting point of the product was 128° to 130° C.

NMR $\delta_{TMS}^{CDCl_3-DMSO-d_6}$ (ppm):
4.50 (2H, s), 6.30 (1H, d), 7.2–8.1 (3H, m), 9.25 (1H, d).

The above 3-iodopropargyl alcohol was prepared by the method described in Bull. Chem. Soc. Jpn., 45, 2611 (1972).

SYNTHESIS EXAMPLE 4

Synthesis of alpha-(3-bromopropargyloxy)-3,5-dichlorobenzoylaminoacetonitrile (Compound No. 43):

Bromine (2.8 g) was added at a time to a solution of 4.0 g of 3,5-dichlorobenzoylaminoacetonitrile in 100 ml of ethyl acetate at room temperature. The mixture was stirred until the color of bromine in the reaction solution disappeared. The reaction solution was cooled to 0° to 5° C. 3-Bromopropargyl alcohol (2.8 g) and 3.5 g of triethylamine were dissolved in 10 ml of ethyl acetate. The solution was added dropwise to the ethyl acetate solution of the bromine compound prepared above under ice cooling. After the addition, the reaction was continued for 30 minutes at room temperature. Triethylamine hydrobromide was separated by filtration, and the filtrate was concentrated under reduced pressure. The residue was purified by silica gel column chromatography. By elution with hexane/ethyl acetate, 4.5 g of alpha-(3-bromopropargyloxy)-3,5-dichlorobenzoylaminoacetonitrile was obtained as a white solid. The yield was 71.2%, and the melting point of the product was 128° to 130° C.

NMR $\delta_{TMS}^{CDCl_3-DMSO-d_6}$ (ppm):
4.37 (2H, s), 6.30 (1H, d), 7.4–8.1 (3H, m), 10.06 (1H, d).

The above 3-bromopropargyl alcohol was prepared by the method described in Bull. Chem. Soc. Jpn., 45, 2611 (1972).

SYNTHESIS EXAMPLE 5

Synthesis of alpha-(1-methylpropargyloxy)-3,5-dimethylbenzoylaminoacetonitrile (Compound No. 79):

Bromine (3.2 g) was added at a time to a solution of 3.8 g of 3,5-dimethylbenzoylaminoacetonitrile in 100 ml of ethyl acetate at room temperature. The mixture was stirred until the color of bromine in the reaction solution disappeared. The reaction solution was cooled to 0° to 5° C. 1-Butyn-3-ol (1.7 g) and 4.1 g of triethylamine were dissolved in 10 ml of ethyl acetate. The solution was added dropwise to the ethyl acetate solution of the bromine compound prepared above under ice cooling. After the addition, the reaction was continued for 30 minutes at room temperature. After the reaction, triethylamine hydrobromide was separated from the reaction mixture by filtration, and the filtrate was concentrated under reduced pressure. The residue was purified by silica gel column chromatography. By elution with hexane/ethyl acetate, 3.6 g of alpha-(1-methylpropargyloxy)-3,5-dimethylbenzoylaminoacetonitrile was obtained as a white solid from the eluate. The yield was 69.6%, and the melting point of the product was 83° to 85° C.

NMR (100 MHz, δ): $\delta_{TMS}^{CDCl_3}$ (ppm):
1.54 (3H, dd), 2.28 (6H, s), 2.62 (1H, t), 4.54 (1H, m), 6.50 (1H, dd), 7.1–7.7 (4H, m).

The following Formulation Examples illustrate the formulation of the paddy herbicide or the agricultural-horticultural fungicide of this invention.

The active compounds in these examples are designated by the compound numbers given in Table 1. All parts are by weight.

FORMULATION EXAMPLE 1

Dust:
Three parts of compound No. 1, 20 parts of diatomaceous earth, 30 parts of terra alba and 47 parts of talc were uniformly pulverized and mixed to obtain 100 parts of a dust.

FORMULATION EXAMPLE 2

Wettable powder:
Thirty parts of compound No. 10, 44 parts of diatomaceous earth, 20 parts of terra alba, 1 part of sodium ligninsulfonate and 2 parts of sodium alkylbenzenesulfonate were uniformly pulverized and mixed to obtain 100 parts of a wettable powder.

FORMULATION EXAMPLE 3

Emulsifiable concentrate:
Forty parts of compound No. 13, 10 parts of cyclohexanone, 30 parts of xylene and 20 parts of Sorpol (a trade name for a surface-active agent produced by Toho Chemical Co., Ltd.) were uniformly mixed to obtain 100 parts of an emulsifiable concentrate.

FORMULATION EXAMPLE 4

Granules:
One part of compound No. 25, 78 parts of bentonite, 20 parts of talc and 1 part of sodium ligninsulfonate were mixed, and kneaded with a moderate amount of water. The mixture was granulated in a conventional manner in an extrusion granulator, and dried to obtain 100 parts of granules.

FORMULATION EXAMPLE 5

Granules:
Seven parts of compound No. 59, 1 part of polyethylene glycol nonyl phenyl ether, 3 parts of polyvinyl alcohol, and 89 parts of clay were uniformly mixed. Water was added, and the mixture was granulated, and dried to obtain 100 parts of granules.

FORMULATION EXAMPLE 6

Dust:

Two parts of compound No. 71, 40 parts of calcium carbonate and 58 parts of clay were uniformly pulverized and mixed to obtain 100 parts of a dust.

FORMULATION EXAMPLE 7

Wettable powder:

Fifty parts of compound No. 77, 40 parts of talc, 5 parts of sodium laurylphosphate and 5 parts of sodium alkylnaphthalenesulfonate to obtain 100 parts of a wettable powder.

FORMULATION EXAMPLE 8

Fifty parts of compound No. 79, 10 parts of sodium ligninsulfonate, 5 parts of sodium alkylnaphthalenesulfonate, 10 parts of white carbon and 25 parts of diatomaceious earth were mixed and pulverized to obtain 100 parts of a wettable powder.

FORMULATION EXAMPLE 9

Flowable composition:

Forty parts of compound No. 88, 3 parts of carboxymethyl cellulose, 2 parts of sodium ligninsulfonate, 1 part of sodium dioctylsulfosuccinate and 54 parts of water were wet-pulverized by a sand grinder to obtain 100 parts of a flowable composition.

The following Test Examples illustrate the herbicidal activity of the compounds of this invention.

TEST EXAMPLE 1

Pre-emergence Test in Paddy Field:

Soil was filled in Wagner pots (1/5000 are), and seeds of barnyard grass (*Echinochloa crus-galli*), broadleaved weeds (*Rotala indica, Lindernia procumbens pyxidaria, Monochoria vaginalis*, etc.), *Scirpus juncoides, Alisma canaliculatum*, and *Cyperus difformis* were sown. The soil in the pots was maintained in the submerged state. Rice seedlings (2- to 3-leaf stage) previously grown were arranged in stocks each consisting of two seedlings. Two stocks were transplanted in each pot, and grown in a greenhouse. One day after the transplantation when the weeds still did not emerge, a granular composition prepared in accordance with Formulation Example 5 using a predetermined amount of each of the test compounds was applied to the pots in the submerged state. Thirty days after the application, the state of occurrence of the weeds and phytotoxicity to rice were examined. The results are shown in Table 2.

The degree of phytotoxicity to the crop and the herbicidal effect on the weeds in Table 2 were determined by comparing the air-dried weight of the crop or each weed with the air-dried weight of the crop or each weed in a non-treated area, and showing the state of occurrence or growth of the crop or the weed on the following scale of 0 to 5. The test compounds are indicated by the compound numbers given in Table 1 (this is the same in the following Test Examples).

| Scale of Evaluation | |
|---|---|
| Rating | Survival rate in terms of the ratio of the air-dried weight to that of the non-treated area |
| 0 | 91–100% |
| 1 | 71–90% |
| 2 | 41–70% |
| 3 | 11–40% |
| 4 | 6–10% |
| 5 | 0–5% |

Control compounds

A: alpha-allyloxy-3-chlorobenzoylaminoacetonitrile (described in GB No. 2,694,786)

B: alpha-allyloxy-3,5-dichlorobenzoylaminoacetonitrile (described in GB No. 2,694,786)

C: Butachlor [2-chloro-2',6'-diethyl-N-(butoxymethyl)acetonitrile]

The weeds in Table 2 are designated by the following abbreviations.

Ec: *Echinochloa crus-galli*
Mv: *Monochoria vaginalis*
Cd: *Cyperus difformis*
Sj: *Scirpus juncoides*
Ac: *Alisma canaliculatum*

TABLE 2

| Test compound | Rate of application (g/a) | Ec | Mv | Cd | Sj | Ac | Phytotoxicity Rice |
|---|---|---|---|---|---|---|---|
| 2 | 50 | 5 | 5 | 5 | 5 | 5 | 0 |
| 4 | " | 5 | 3 | 5 | 5 | 5 | 0 |
| 5 | " | 5 | 5 | 5 | 3 | 5 | 0 |
| 7 | " | 5 | 2 | 5 | 5 | 5 | 0 |
| 9 | " | 5 | 4 | 5 | 5 | 5 | 0 |
| 10 | " | 5 | 3 | 5 | 5 | 5 | 0 |
| 12 | " | 5 | 4 | 5 | 5 | 5 | 0 |
| 21 | " | 5 | 5 | 5 | 5 | 5 | 1 |
| 22 | " | 5 | 5 | 5 | 5 | 5 | 0 |
| 24 | " | 5 | 5 | 5 | 5 | 5 | 0 |
| 25 | " | 5 | 5 | 5 | 5 | 5 | 1 |
| 27 | " | 5 | 5 | 4 | 5 | 4 | 1 |
| 28 | " | 5 | 4 | 5 | 5 | 5 | 0 |
| 29 | " | 5 | 5 | 5 | 5 | 4 | 0 |
| 32 | " | 5 | 5 | 5 | 5 | 5 | 1 |
| 35 | " | 5 | 5 | 5 | 5 | 4 | 0 |
| 37 | " | 5 | 5 | 5 | 5 | 4 | 1 |
| 40 | " | 5 | 5 | 5 | 5 | 5 | 0 |
| 41 | " | 5 | 5 | 5 | 5 | 5 | 0 |
| 42 | " | 3 | 3 | 4 | 5 | 5 | 0 |
| 43 | " | 5 | 5 | 5 | 5 | 5 | 0 |
| 44 | " | 5 | 5 | 5 | 5 | 5 | 0 |
| 47 | " | 5 | 5 | 4 | 5 | 5 | 1 |
| 48 | " | 5 | 5 | 5 | 5 | 5 | 0 |
| 51 | " | 5 | 5 | 5 | 5 | 5 | 0 |
| 53 | " | 5 | 5 | 5 | 3 | 5 | 0 |
| 55 | " | 2 | 5 | 5 | 5 | 5 | 0 |
| 56 | " | 5 | 5 | 5 | 5 | 5 | 1 |
| 57 | " | 5 | 5 | 5 | 5 | 5 | 1 |
| 58 | " | 5 | 5 | 5 | 5 | 5 | 1 |
| 62 | " | 5 | 5 | 5 | 5 | 5 | 1 |
| 67 | " | 5 | 5 | 5 | 5 | 5 | 1 |
| 68 | " | 5 | 5 | 5 | 5 | 5 | 0 |
| 69 | " | 5 | 5 | 5 | 5 | 5 | 0 |
| 70 | " | 5 | 5 | 5 | 5 | 5 | 0 |
| 71 | " | 5 | 5 | 5 | 5 | 5 | 0 |
| 74 | " | 5 | 5 | 5 | 5 | 5 | 1 |
| 75 | " | 5 | 5 | 5 | 5 | 5 | 0 |
| 76 | " | 5 | 5 | 5 | 5 | 5 | 0 |
| 77 | " | 5 | 5 | 5 | 5 | 5 | 0 |
| 79 | " | 5 | 5 | 5 | 5 | 5 | 1 |
| 80 | " | 5 | 5 | 5 | 5 | 4 | 0 |
| 84 | " | 5 | 5 | 5 | 5 | 4 | 1 |
| 90 | " | 5 | 5 | 5 | 5 | 5 | 0 |
| A | " | 3 | 3 | 5 | 3 | 3 | 2 |
| B | " | 3 | 5 | 5 | 4 | 3 | 2 |
| C | " | 4 | 5 | 3 | 5 | 4 | 2 |

TEST EXAMPLE 2

Post-emergence Test in Paddy Field:

Soil was filled in Wagner pots (1/5000 are), and seeds of barnyard grass (*Echinochloa crus-galli*), broadleaved weeds (*Rotala indica, Lindernia procumbens pyxidaria, Monochoria vaginalis*, etc.), *Scirpus juncoides, Alisma canaliculatum*, and *Cyperus difformis* were sown, and the soil in the pots was maintained in the submerged state. Rice seedlings (2- to 3-leaf stage) previously grown were arranged in stocks each consisting of two seedlings. Two stocks were transplanted in each pot, and grown in a greenhouse. Twelve days after the transplantation when the weeds were in the growing stage, a granular composition prepared in accordance with Formulation Example 4 using a predetermined amount of each of the test compounds was applied to the pots in the submerged state. Thirty days after the application, the state of occurrence of the weeds and phytotoxicity to rice were examined. The results are shown in Table 3.

The degree of phytotoxicity to the crop and the herbicidal effect on the weeds in Table 3 were determined in accordance with the method shown in Test Example 1.

The control compounds used were as follows:
A: same as in Test Example 1
B: same as in Test Example 1
D: Benthiocarb (S-p-chlorobenzyl diethylthiocarbamate)

The weeds in Table 3 are indicated by the same abbreviations as in Test Example 1.

TABLE 3

| Test compound | Rate of application (g/a) | Herbicidal effect | | | | | Phytotoxicity Rice |
|---|---|---|---|---|---|---|---|
| | | Ec | Mv | Cd | Sj | Ac | |
| 2 | 50 | 5 | 4 | 3 | 3 | 3 | 0 |
| 3 | " | 3 | 5 | 5 | 3 | 5 | 0 |
| 9 | " | 4 | 4 | 4 | 3 | 4 | 0 |
| 10 | " | 5 | 3 | 5 | 4 | 5 | 0 |
| 12 | " | 5 | 4 | 3 | 3 | 4 | 0 |
| 21 | " | 5 | 5 | 4 | 2 | 3 | 0 |
| 22 | " | 5 | 5 | 5 | 2 | 3 | 0 |
| 25 | " | 5 | 5 | 3 | 2 | 2 | 0 |
| 27 | " | 5 | 4 | 4 | 3 | 4 | 0 |
| 30 | " | 5 | 4 | 4 | 3 | 4 | 0 |
| 32 | " | 5 | 4 | 4 | 3 | 4 | 0 |
| 33 | " | 5 | 5 | 4 | 3 | 4 | 0 |
| 37 | " | 5 | 5 | 4 | 3 | 4 | 0 |
| 41 | " | 5 | 5 | 4 | 3 | 4 | 0 |
| 43 | " | 5 | 5 | 4 | 3 | 4 | 0 |
| 55 | " | 5 | 5 | 4 | 3 | 4 | 0 |
| 56 | " | 5 | 5 | 3 | 3 | 3 | 0 |
| 57 | " | 5 | 4 | 4 | 1 | 2 | 0 |
| 62 | " | 5 | 5 | 3 | 2 | 4 | 0 |
| 70 | " | 5 | 4 | 4 | 3 | 4 | 0 |
| 71 | " | 5 | 5 | 4 | 3 | 4 | 0 |
| 74 | " | 5 | 4 | 4 | 4 | 4 | 0 |
| 75 | " | 5 | 4 | 4 | 4 | 4 | 0 |
| 76 | " | 5 | 5 | 3 | 3 | 4 | 0 |
| 77 | " | 5 | 5 | 3 | 3 | 4 | 0 |
| 79 | " | 5 | 5 | 3 | 3 | 4 | 0 |
| A | " | 3 | 2 | 3 | 1 | 1 | 0 |
| B | " | 3 | 2 | 3 | 1 | 1 | 0 |
| D | " | 4 | 5 | 4 | 3 | 3 | 0 |

The results given in Tables 2 and 3 demonstrate that the group of compounds of this invention exhibit a broad range of herbicidal activity on various weeds detrimental to rice paddies not only by pre-emergence treatment but also by treatment during the growing period at which time the conventional herbicides did not show significant herbicidal effects, and that these compounds hardly cause phytotoxicity to rice.

The control compounds A and B, i.e. alpha-allyloxy-3-chlorobenzoylaminoacetonitrile and alpha-allyloxy-3,5-dichlorobenzoylaminoacetonitrile disclosed in GB No. 2,694,786, showed phytotoxicity to rice in the pre-emergence test in a paddy field and therefore had no selectivity as a paddy herbicide, whereas the compounds of the present invention showed excellent selectivity with no phytotoxicity to rice.

The following Test Examples show the fungicidal activity of the compounds of this invention. As regards late blight and downy mildew, the compounds of this invention were compared with amide-substituted alyloxyacetonitrile derivatives (control compounds A and B) which seem to have a structure relatively close to the compounds of this invention among the compounds disclosed in GB No. 2,694,786.

TEST EXAMPLLE 3

Test for controlling potato late blight (preventive effect):

Potato (variety: "Danshaku", height about 25 cm) was grown in pots in a greenhouse. A wettable powder was prepared by using each of the test compounds in accordance with the method of Formulation Example 2, and diluting it with water to a predetermined concentration. The chemical was sprayed by a spray gun (1.0 kg/cm$^2$) at a rate of 50 ml per three pots, and then air dried. A zoospore suspension was prepared from *Phytophthora infestans* cultivated in advance for 7 days on a potato slice. The suspension was inoculated in the potato plants by spraying. The plants were maintained for 6 days at a temperature of 17° to 19° C. and a humidity of more than 95%, and then the degree of formation of lesions was examined.

The ratio of the area of lesions was observed and evaluated for each leaf, and the disease rate was determined. For each area, the disease index was calculated in accordance with the following equation.

$$\text{Disease index} = \frac{4n_4 + 2n_3 + 2n_2 + 1n_1 + 0n_0}{\Sigma N}$$

The scale of evaluation was as follows.

| Disease rate | Ratio of the area of lesions |
|---|---|
| 0 | 0% |
| 1 | 1–5% |
| 2 | 6–25% |
| 3 | 26–50% |
| 4 | 51% or more |

$n_0$: the number of leaves having a disease rate of 0
$n_1$: the number of leaves having a disease rate of 1
$n_2$: the number of leaves having a disease rate of 2
$n_3$: the number of leaves having a disease rate of 3
$n_4$: the number of leaves having a disease rate of 4

The results are shown in Table 4.
The control compounds were as follows:
A: same as in Test Example 1
B: same as in Test Example 1
E: Zinc ethylenebis(dithiocarbamate)
F: tetrachloroisophthalonitrile
E and F are commercial chemicals for controlling potato late blight and cucumber downy mildew.

TABLE 4

| Test compound | Concentration of the active ingredient (ppm) | Disease index | Phytotoxicity |
|---|---|---|---|
| 2 | 200 | 0.55 | None |
| 4 | " | 0.50 | " |
| 5 | " | 0 | " |
| 12 | " | 0.42 | " |
| 21 | " | 0.31 | " |

TABLE 4-continued

| Test compound | Concentration of the active ingredient (ppm) | Disease index | Phytotoxicity |
|---|---|---|---|
| 22 | " | 0 | " |
| 23 | " | 0 | " |
| 24 | " | 0 | " |
| 25 | " | 0 | " |
| 26 | " | 0 | " |
| 27 | " | 0 | " |
| 31 | " | 0 | " |
| 32 | " | 0 | " |
| 34 | " | 0 | " |
| 35 | " | 0 | " |
| 36 | " | 0 | " |
| 37 | " | 0 | " |
| 39 | " | 0 | " |
| 43 | " | 0 | " |
| 49 | " | 0.25 | " |
| 51 | " | 0 | " |
| 52 | " | 0 | " |
| 53 | " | 0 | " |
| 55 | " | 0 | " |
| 62 | " | 0.56 | " |
| 67 | " | 0.35 | " |
| 68 | " | 0 | " |
| 69 | " | 0 | " |
| 71 | " | 0 | " |
| 72 | " | 0.20 | " |
| 74 | " | 0 | " |
| 75 | " | 0 | " |
| 76 | " | 0 | " |
| 77 | " | 0 | " |
| 78 | " | 0 | " |
| 79 | " | 0 | " |
| 80 | " | 0 | " |
| 81 | " | 0 | " |
| 83 | " | 0.12 | " |
| 84 | " | 0 | " |
| 85 | " | 0 | " |
| 86 | " | 0 | " |
| 87 | " | 0 | " |
| 89 | " | 0 | " |
| 90 | " | 0 | " |
| A | " | 0.60 | " |
| B | " | 0.43 | " |
| E | " | 2.02 | " |
| F | " | 1.75 | " |
| Non-treated area | — | 3.65 | — |

TABLE 5

| Test compound | Concentration of the active ingredient (ppm) | Disease index | Phytotoxicity |
|---|---|---|---|
| 2 | 200 | 0.58 | None |
| 4 | " | 0.42 | " |
| 5 | " | 0 | " |
| 12 | " | 0.45 | " |
| 22 | " | 0.12 | " |
| 23 | " | 0.05 | " |
| 24 | " | 0.24 | " |
| 25 | " | 0 | " |
| 27 | " | 0 | " |
| 28 | " | 0.05 | " |
| 29 | " | 0 | " |
| 30 | " | 0 | " |
| 32 | " | 0 | " |
| 33 | " | 0.13 | " |
| 34 | " | 0 | " |
| 35 | " | 0.10 | " |
| 36 | " | 0.12 | " |
| 37 | " | 0 | " |
| 43 | " | 0 | " |
| 51 | " | 0 | " |
| 52 | " | 0 | " |
| 53 | " | 0.08 | " |
| 54 | " | 0.14 | " |
| 55 | " | 0 | " |
| 62 | " | 0.40 | " |
| 67 | " | 0.64 | " |
| 68 | " | 0 | " |
| 69 | " | 0.13 | " |
| 71 | " | 0 | " |
| 72 | " | 0.36 | " |
| 74 | " | 0 | " |
| 75 | " | 0.12 | " |
| 76 | " | 0 | " |
| 77 | " | 0 | " |
| 78 | " | 0 | " |
| 79 | " | 0 | " |
| 80 | " | 0 | " |
| 81 | " | 0.06 | " |
| 83 | " | 0.20 | " |
| 84 | " | 0 | " |
| 85 | " | 0 | " |
| 86 | " | 0 | " |
| 87 | " | 0.10 | " |
| 89 | " | 0.27 | " |
| 90 | " | 0 | " |
| A | " | 0.48 | " |
| B | " | 0.53 | " |
| E | " | 3.42 | " |
| F | " | 3.35 | " |
| Non-treated area | — | 3.23 | — |

TEST EXAMPLE 4

Test for controlling potato late blight (curative effect):

A zoospore suspension of *Phytophthora infestans* prepared as in Test Example 3 was inoculated in potato (variety: "Danshaku", height about 25 cm) grown in pots in a greenhouse by spraying. The plants were maintained for 20 hours at a temperature of 17° to 19° C. and a humidity of 95%. Then, a chemical in a predetermined concentration (obtained by preparing a wettable powder from each of the test compounds in accordance with Formulation Example 2, and diluting it to a predetermined concentration) was sprayed onto the plants by a spray gun (1.0 kg/cm²). After air-drying, the plants were again maintained for 5 days at a temperature of 17° to 19° C. and a humidity of more than 95%, and the degree of formation of lesions was examined.

The scale of evaluation and the disease index were the same as in Test Example 3. The results are shown in Table 5.

The control compounds used were A, B, E and F which were the same as in Test Example 3.

TEST EXAMPLE 5

Test for controlling cucumber downy mildew (preventive effect):

A chemical in a predetermined concentration (obtained by preparing a wettable powder of each of the test compounds in accordance with the method of Formulation Example 2, and diluting it with water to a predetermined concentration) was sprayed onto cucumber (variety: "Sagami Hanshiro"; in the stage where two main leaves developed) at a rate of 30 ml per three pots, and air dried. *Pseudoperonospora cubensis* was sampled from the lesions of cucumber leaves infected with downy mildew, and formed into a spore suspension by using deionized water. The suspension was inoculated in the cucumber plants in the pots by spraying. The pots were immediately maintained for 24 hours at a temperature of 18° to 20° C. and a humidity of more than 95%, and then transferred to a greenhouse (room temperature 18° to 27° C.). Seven days later, the degree of formation of lesions was examined. The scale of evaluation and the disease index were as in Test Example 3. The results are shown in Table 6.

The control compounds used were A, B, E and F which were the same as in Test Example 3.

TABLE 6

| Test compound | Concentration of the active ingredient (ppm) | Disease index | Phytotoxicity |
| --- | --- | --- | --- |
| 4 | 200 | 0 | None |
| 5 | " | 0 | " |
| 12 | " | 0.12 | " |
| 22 | " | 0 | " |
| 23 | " | 0 | " |
| 24 | " | 0 | " |
| 25 | " | 0 | " |
| 26 | " | 0 | " |
| 27 | " | 0 | " |
| 28 | " | 0 | " |
| 29 | " | 0 | " |
| 30 | " | 0 | " |
| 32 | " | 0 | " |
| 33 | " | 0 | " |
| 34 | " | 0 | " |
| 35 | " | 0 | " |
| 36 | " | 0 | " |
| 37 | " | 0 | " |
| 39 | " | 0 | " |
| 43 | " | 0 | " |
| 49 | " | 0 | " |
| 51 | " | 0 | " |
| 52 | " | 0 | " |
| 53 | " | 0 | " |
| 57 | " | 0.34 | " |
| 62 | " | 0.10 | " |
| 65 | " | 0.25 | " |
| 67 | " | 0 | " |
| 68 | " | 0 | " |
| 69 | " | 0 | " |
| 71 | " | 0 | " |
| 72 | " | 0 | " |
| 74 | " | 0 | " |
| 75 | " | 0 | " |
| 76 | " | 0 | " |
| 77 | " | 0 | " |
| 78 | " | 0 | " |
| 79 | " | 0 | " |
| 80 | " | 0 | " |
| 81 | " | 0 | " |
| 83 | " | 0 | " |
| 84 | " | 0 | " |
| 85 | " | 0 | " |
| 86 | " | 0 | " |
| 87 | " | 0 | " |
| 89 | " | 0 | " |
| 90 | " | 0 | " |
| A | " | 0.76 | " |
| B | " | 0.66 | " |
| E | " | 1.35 | " |
| F | " | 1.04 | " |
| Non-treated area | — | 4.00 | — |

TEST EXAMPLE 6

Test for controlling cucumber downy mildew (curative effect):

A zoospore suspension of *Pseudoperonospora cubensis* was prepared and sprayed onto the same cucumber plants as used in Test Example 5 to inoculate the fungus. The plants were maintained for 24 hours at a temperature of 18° to 20° C. and a humidity of more than 95%. A chemical in a predetermined concentration (obtained by preparing a wettable powder of each of the test compounds by the same method as in Formulation Example 2 and diluting it with water to a predetermined concentration) was sprayed onto the plants by means of a spray gun (1.0 kg/cm$^2$) at a rate of 30 ml per three pots). The pots were then transferred to a greenhouse (temperature 18° to 27° C.), and six days later, the degree of formation of lesions was examined.

The scale of evaluation and the disease index were the same as in Test Example 3. The results are shown in Table 7.

The control compounds used were A, B, E and F which were the same as in Test Example 3.

TABLE 7

| Test compound | Concentration of the active ingredient (ppm) | Disease index | Phytotoxicity |
| --- | --- | --- | --- |
| 2 | 200 | 0.24 | None |
| 4 | " | 0.15 | " |
| 5 | " | 0 | " |
| 7 | " | 0.45 | " |
| 9 | " | 0.38 | " |
| 12 | " | 0 | " |
| 22 | " | 0 | " |
| 24 | " | 0 | " |
| 25 | " | 0 | " |
| 27 | " | 0 | " |
| 28 | " | 0 | " |
| 29 | " | 0 | " |
| 30 | " | 0 | " |
| 32 | " | 0 | " |
| 33 | " | 0 | " |
| 34 | " | 0 | " |
| 36 | " | 0 | " |
| 43 | " | 0 | " |
| 44 | " | 0.32 | " |
| 51 | " | 0 | " |
| 52 | " | 0 | " |
| 53 | " | 0 | " |
| 54 | " | 0 | " |
| 55 | " | 0 | " |
| 65 | " | 0.21 | " |
| 67 | " | 0 | " |
| 68 | " | 0 | " |
| 69 | " | 0.08 | " |
| 71 | " | 0 | " |
| 72 | " | 0.12 | " |
| 74 | " | 0 | " |
| 75 | " | 0 | " |
| 76 | " | 0 | " |
| 77 | " | 0 | " |
| 78 | " | 0 | " |
| 79 | " | 0 | " |
| 80 | " | 0 | " |
| 81 | " | 0 | " |
| 83 | " | 0 | " |
| 84 | " | 0 | " |
| 85 | " | 0 | " |
| 86 | " | 0 | " |
| 87 | " | 0 | " |
| 89 | " | 0 | " |
| 90 | " | 0 | " |
| A | " | 0.95 | " |
| B | " | 0.80 | " |
| E | " | 3.74 | " |
| F | " | 3.80 | " |
| Non-treated area | — | 3.65 | — |

The results given in Tables 4, 5, 6 and 7 demonstrate that the compounds of this invention showed a preventive effect at very low dosages on potato late blight and cucumber downy mildew than in the case of zinc ethylenebis(dithiocarbamate) or tetrachloroisophthalonitrile now commercially available and widely used, and also had a curative effect which the above two commercial chemicals do not possess.

It is also clear that the compounds of this invention has an excellent control effect which cannot be anticipated from the compounds disclosed in GB No. 2,694,786, i.e. alpha-allyloxy-3-chlorobenzoylaminoacetonitrile and alpha-allyloxy-3,5-dichlorobenzoylaminoacetonitrile.

TEST EXAMPLE 7

Test for controlling seedling damping off of sugar beet:

A dust of each of the test compounds prepared in accordance with the method of Formulation Example 1 was well mixed with 1 kg of steam-sterilized soil so that the content of the active ingredient became a predetermined value. The mixture was filled in an unglazed pot having a diameter of 18 cm, and 20 seeds of sugar beet (variety: "Monomidori") were sown. The pots was placed in a greenhouse (18° to 28° C.) for 3 days, and a zoospore suspension (about $5 \times 10^4$ cells/ml) of *Aphanomyces cochlioides* separately cultivated was inoculated at a rate of 50 ml/pot in the surface of the soil in the pot in which the beet seeds had been sown. On the 12th day after the sowing, the damping off of the beet seedlings was examined. The test was carried out through 3 replicates, and the results are shown in Table 8 by average values.

$$\text{Control rate (\%)} = \frac{\text{Number of sound seedlings in each treated area}}{\text{Number of seedlings examined in each treated area}} \times 100$$

The control compounds used were as follows:
A: same as in Test Example 3
B: same as in Test Example 3
G: 3-hydroxy-5-methylisoxazole (commercial controlling agent for beet damping off)

TABLE 8

| Test compound | Rate of application (g/a) | Control rate (%) | Phytotoxicity |
|---|---|---|---|
| 4 | 30 | 94 | None |
| 5 | " | 100 | " |
| 12 | " | 91 | " |
| 23 | " | 100 | " |
| 24 | " | 100 | " |
| 25 | " | 100 | " |
| 28 | " | 83 | " |
| 31 | " | 97 | " |
| 32 | " | 100 | " |
| 35 | " | 88 | " |
| 36 | " | 100 | " |
| 43 | " | 100 | " |
| 48 | " | 87 | " |
| 49 | " | 92 | " |
| 51 | " | 100 | " |
| 52 | " | 100 | " |
| 53 | " | 96 | " |
| 55 | " | 100 | " |
| 56 | " | 100 | " |
| 58 | " | 95 | " |
| 60 | " | 100 | " |
| 62 | " | 90 | " |
| 66 | " | 98 | " |
| 68 | " | 100 | " |
| 69 | " | 100 | " |
| 71 | " | 100 | " |
| 72 | " | 100 | " |
| 74 | " | 100 | " |
| 76 | " | 100 | " |
| 77 | " | 100 | " |
| 79 | " | 100 | " |
| 82 | " | 98 | " |
| 86 | " | 94 | " |
| A | " | 28 | " |
| B | " | 45 | " |
| G | " | 86 | " |
| Non-treated | — | 0 | — |

TABLE 8-continued

| Test compound | Rate of application (g/a) | Control rate (%) | Phytotoxicity |
|---|---|---|---|

The results given in Table 8 demonstrate that the compounds of this invention showed an apparently higher control effect on beet damping off induced by *Aphanomyces cochlioides* than 3-hydroxy-5-methylisoxazole (hymexazole) now commercially available. Furthermore it is clear that the compounds of this invention have an excellent control effect which cannot be anticipated from the compounds disclosed in GB No. 2,694,786, i.e. alpha-allyloxy-3-chlorobenzoylaminoacetonitrile and alpha-allyloxy-3,5-dichlorobenzoylaminoacetonitrile.

As is clearly seen from the foregoing description, the substituted propargyloxyacetonitrile derivatives of this invention, when used as a paddy herbicide, shows an excellent herbicidal effect with a broad range of the suitable time of application which cannot be expected from the conventional herbicides, and when used as an agricultural-horticultural fungicide, shows both a preventive and a curative effect at very low dosages and concentrations in which conventional commercial chemicals cannot be expected to be efficacious. Hence, agricultural chemicals comprising the substituted propargyloxyacetonitrile derivatives of this invention are very useful as herbicides and agricultural-horticultural fungicides.

In the methods previously proposed for the production of acetonitrile derivatives, the hydrolysis reaction of the nitrile group occurs in the halogenation step to form carbamoyl derivatives. Hence, these methods must involve steps of, for example, alkoxylating the halogen and then dehydrating the carbamoyl group to otain the desired acetonitrile derivatives, and the yields of the desired compounds are low. In contrast, in the process of this invention to produce the substituted propargyloxyacetonitrile derivatives of this invention, the nitrile group does not undergo hydrolysis in the halogenation step, and by simply adding the reaction material to the resulting halogenated intermediate, the final products can be obtained easily in high yields by a substantially shorter process.

What is claimed is:

1. A substituted propargyloxyacetonitrile derivative represented by the general formula (I)

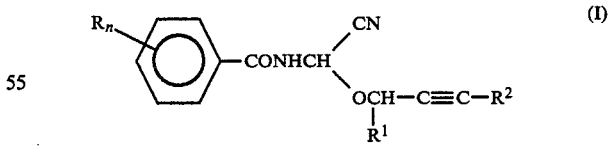

wherein R represents a hydrogen atom, a halogen atom, a lower alkyl group, a lower haloalkyl group, a lower alkoxy group, a methylenedioxy group, a nitro group or a cyano group, n represents an integer of 1 to 5 and when n is an integer of 2 or more, R's may be identical or different, $R^1$ represents a hydrogen atom or a lower alkyl group, and $R^2$ represents a hydrogen atom, a lower alkyl group, a lower haloalkyl group or a halogen atom, provided that $R^1$ and $R^2$ are not simultaneously hydrogen atoms.

2. The compound of claim 1 wherein $R^1$ is a hydrogen atom and $R^2$ is a halogen atom.

3. The compound of claim 1 wherein $R^1$ is a hydrogen atom, and $R^2$ is a methyl group.

4. The compound of claim 1 wherein $R^1$ is a methyl group, and $R^2$ is a hydrogen atom.

5. The compound of claim 1 wherein R is a halogen atom or a methyl group, n is 1 to 4, $R^1$ is a hydrogen atom, and $R^2$ is a methyl group.

6. The compound of claim 1 wherein R is a halogen atom or a methyl group, n is 1 to 4, $R^1$ is a methyl group, and $R^2$ is a hydrogen atom.

7. A process for producing a substituted propargyloxyacetonitrile derivative represented by the general formula

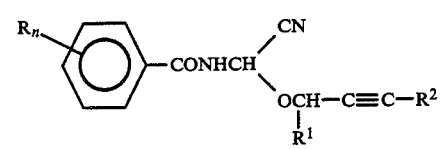

wherein R represents a hydrogen atom, a halogen atom, a lower alkyl group, a lower haloalkyl group, a lower alkoxy group, a methylenedioxy group, a nitro group or a cyano group, n represents an integer of 1 to 5 and when n is an integer of 2 or more, R's may be identical or different, $R^1$ represents a hydrogen atom or a lower alkyl group, and $R^2$ represents a hydrogen atom, a lower alkyl group, a lower haloalkyl group or a halogen atom, provided that $R^1$ and $R^2$ are not simultaneously hydrogen atoms, which comprises reacting an acid chloride represented by the following general formula (II)

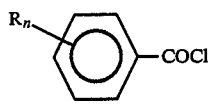

wherein R and n are as defined hereinabove, with aminoacetonitrile to obtain an acylaminoacetonitrile represented by the general formula (III)

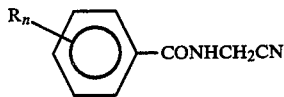

wherein R and n are as defined above, treating the resulting compound with a halogenating agent to obtain an intermediate represented by the following general formula (IV)

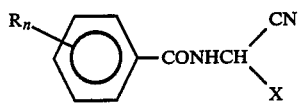

wherein R and n are as defined above, and X represents a halogen atom,
and reacting the intermediate with a substituted propargyl alcohol of the general formula (V)

$$R^2-C{\equiv}C-CH-OH \atop R^1 \qquad (V)$$

wherein $R^1$ and $R^2$ are as defined.

8. The process of claim 7 wherein R is a halogen atom or a methyl group, n is 1 to 4, $R^1$ is a hydrogen atom, and $R^2$ is a halogen atom or a methyl group.

9. The process of claim 7 wherein R is a halogen atom or a methyl group, n is 1 to 4, $R^1$ is a hydrogen atom, and $R^2$ is a methyl group.

10. A herbicide comprising at least one substituted propargyloxyacetonitrile derivative represented by the general formula (I)

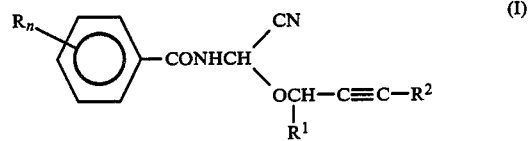

wherein R represents a hydrogen atom, a halogen atom, a lower alkyl group, a lower haloalkyl group, a lower alkoxy group, a methylenedioxy group, a nitro group or a cyano group, n represents an integer of 1 to 5 and when n is an integer of 2 or more, R's may be identical or different, $R^1$ represents a hydrogen atom or a lower alkyl group, and $R^2$ represents a hydrogen atom, a lower alkyl group, a lower haloalkyl group or a halogen atom, provided that $R^1$ and $R^2$ are not simultaneously hydrogen atoms,
as an active ingredient and a liquid or solid diluent or carrier, and/or a surface-active agent.

11. The herbicide of claim 10 wherein the proportion of the compound of general formula (I) is 1 to 90% by weight.

12. An agricultural-horticultural fungicide comprising at least one substituted propargyloxyacetonitrile derivative represented by the general formula (I)

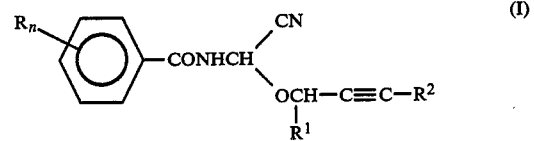

wherein R represents a hydrogen atom, a halogen atom, a lower alkyl group, a lower haloalkyl group, a lower alkoxy group, a methylenedioxy group, a nitro group or a cyano group, n represents an integer of 1 to 5 and when n is an integer of 2 or more, R's may be identical or different, $R^1$ represents a hydrogen atom or a lower alkyl group, and $R^2$ represents a hydrogen atom, a lower alkyl group, a lower haloalkyl group or a halogen atom, provided that $R^1$ and $R^2$ are not simultaneously hydrogen atoms,
as an active ingredient and a liquid or solid diluent or carrier, and/or a surface-active agent.

13. The fungicide of claim 12 wherein the proportion of the compound of general formula is 1 to 90% by weight.

14. A method of controlling weeds which comprising applying the compound of claim 1 to the weeds or a habitat thereof.

15. A method of controlling weeds, which comprises applying the herbicide of claim 10 or 11 to the weeds or a habitat thereof.

16. A method of controlling a plant disease, which comprises applying the compound of claim 1 to a plant pathogenic fungus or a habitat thereof.

17. A method of controlling a plant disease, which comprises applying the fungicide of claim 12 or 13 to a plant pathogenic fungus or a habitat thereof.

18. The method of any one of claim 14, 15, 16 and 17 wherein the compound of general formula (I) is applied as an active ingredient at a rate of 0.1 to 10 kg/ha.

* * * * *